United States Patent
Jung et al.

(10) Patent No.: US 8,345,818 B2
(45) Date of Patent: Jan. 1, 2013

(54) TOMOSYNTHESIS SYSTEM FOR DIGITAL X-RAY IMAGING AND METHOD OF CONTROLLING THE SAME

(75) Inventors: Sun Shin Jung, Ansan (KR); Dae Ho Kim, Ansan (KR); Seung Kwon Seol, Seoul (KR); Seung Oh Jin, Ansan (KR)

(73) Assignee: Korea Electrotechnology Research Institute, Changwon (KR)

( * ) Notice: Subject to any disclaimer, the term of this patent is extended or adjusted under 35 U.S.C. 154(b) by 219 days.

(21) Appl. No.: 12/956,712

(22) Filed: Nov. 30, 2010

(65) Prior Publication Data

US 2012/0020450 A1     Jan. 26, 2012

(30) Foreign Application Priority Data

Jul. 22, 2010 (KR) .................. 10-2010-0071044

(51) Int. Cl.
    *A61B 6/00*     (2006.01)
(52) U.S. Cl. ............................................. 378/21

(58) Field of Classification Search .................... 378/16, 378/21, 137, 138
See application file for complete search history.

(56) References Cited

FOREIGN PATENT DOCUMENTS

| | | | |
|---|---|---|---|
| JP | 2007-282740 A | 11/2007 |
| JP | 2009-142349 A | 7/2009 |
| JP | 2010-035812 A | 2/2010 |

*Primary Examiner* — Courtney Thomas

(57) ABSTRACT

Disclosed herein are a tomosynthesis system for digital X-ray imaging and a method of controlling the tomosynthesis system. The tomosynthesis system includes an X-ray source, a detector, and a terminal. The X-ray source continuously moves during a scan period, and maintains a uniform X-ray focus in each capture section in which capture is performed by adjusting the direction of an emitted electron beam. The detector detects an image of X-rays having passed through an area of interest of an object in the capture section. The terminal controls the adjustment of the direction of the electron beam, creates a three-dimensional (3D) X-ray image by synthesizing detected X-ray images, and then displays the 3D X-ray image.

14 Claims, 7 Drawing Sheets

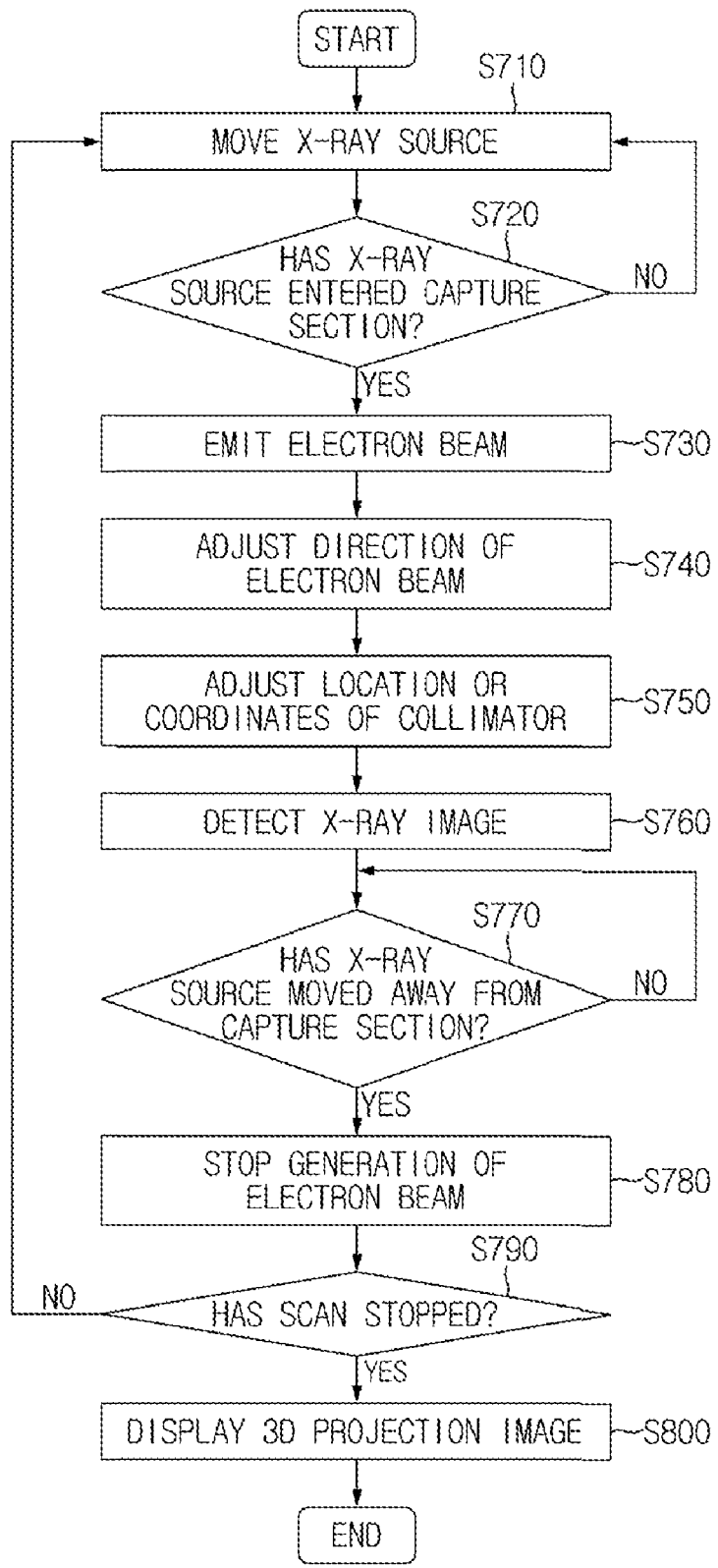

TOMOSYNTHESIS SYSTEM FOR DIGITAL X-RAY IMAGING AND METHOD OF CONTROLLING THE SAME

BACKGROUND OF THE INVENTION

1. Field of the Invention

The present invention relates to a tomosynthesis system for digital X-ray imaging and a method of controlling the system.

2. Description of the Related Art

In general, medical or industrial X-ray imaging devices which see through a patient's body or an object and capture regions of the body or object using the penetrative property of X-rays are being widely used.

Although an analog film method had been used conventionally, a digital method using a semiconductor flat-panel detector, in place of the analog film method, has been widely used recently.

With regard to the migration to the digital method, a digital imaging apparatus capable of simply acquiring two-dimensional (2D) projection images is accompanied by the problem that it is difficult to make diagnoses when lesions are covered by bodily tissues. Therefore, tomosynthesis systems which capture an object at various angles and synthesize tomograms, thereby considerably improving diagnosis performance, have been developed.

Such a tomosynthesis system detects X-ray images at various angles, creates a 3D projection image of, for example, a patient's breast, and displays the created 3D projection image.

However, the tomosynthesis system is configured such that an X-ray source should move and stop repeatedly, rather than continuously moving, in order to capture X-ray images at various angles. That is, the tomosynthesis system employs a step-and-shoot method in which an X-ray source stops at a capture angle and then captures an X-ray image, moves to another capture angle, and then stops at the latter capture angle and then captures another X-ray image.

Even if an X-ray source continuously moves, blur (which makes the contour of an image indistinct) occurs in images formed in a stationary detector due to the movement of the X-ray source during the exposure time of each X-ray capture, thereby deteriorating the quality of the images.

FIG. 1 is an exemplary diagram illustrating the principle of capturing which is performed while the X-ray source of a conventional tomosynthesis system continuously moves.

As shown in FIG. 1, in the case where an X-ray source continuously moves, the X-ray source moves by $\Delta X_S$ during exposure time $\Delta t$, and an X-ray focus also moves as the X-ray source moves. Accordingly, an image formed in the detector also moves by $\Delta X_D$ as the X-ray source moves, so that blur occurs.

In particular, the blur of images increases proportional to the speed of the X-ray source and the exposure time of X-rays.

Since the X-ray source moves over a predetermined angle while repeatedly moving and stopping as described above, mechanical instability occurs and the scan time may only limitedly be reduced. In particular, when the number of captures is large, the scan time increases because of a large number of times the X-ray source moves and stops, thereby increasing patients' pain and inconvenience.

SUMMARY OF THE INVENTION

Accordingly, the present invention has been made keeping in mind the above problems occurring in the prior art, and an object of the present invention is to provide a tomosynthesis system for digital X-ray imaging and a method of controlling the system, which is capable of maintaining a uniform X-ray focus in each section by adjusting the direction of an electron beam emitted by the electron gun of the X-ray source while the X-ray source continuously moves.

In order to accomplish the above object, the present invention provides a tomosynthesis system for digital X-ray imaging, including an X-ray source configured to continuously move during a scan period and to maintain a uniform X-ray focus in each capture section in which capture is performed by adjusting the direction of an emitted electron beam; a detector for detecting an image of X-rays having passed through an area of interest of an object in the capture section; and a terminal for controlling the adjustment of direction of the electron beam, and creating a three-dimensional (3D) X-ray image by synthesizing detected X-ray images and then displaying the 3D X-ray image.

The X-ray source may include an electron gun for emitting the electron beam when the X-ray source enters the capture section; a deflection unit for adjusting the direction of the emitted electron beam; and an X-ray target for enabling the electron beam to be focused at a predetermined X-ray focus and radiate the X-rays.

The deflection unit may be any one of a device using an electric or magnetic field method and a device using a combination thereof.

The terminal may control the direction of the electron beam based on the speed, exposure time and tube voltage of the X-ray source.

In order to accomplish the above object, the present invention provides a tomosynthesis system for digital X-ray imaging, including an X-ray source configured to continuously move during a scan period and to maintain a uniform X-ray focus in each capture section in which capture is performed by adjusting the direction of an emitted electron beam; a collimator configured such that it is controlled by moving it based on a preset location or preset coordinates in the capture section; a detector for detecting an image of X-rays having passed through an area of interest of an object in the capture section; and a terminal for controlling the adjustment of direction of the electron beam, and creating a 3D X-ray image by synthesizing detected X-ray images and then displaying the 3D X-ray image.

The collimator may enable the X-rays to enter the area of interest of the object by controlling gaps between blades.

The X-ray source may include an electron gun for emitting the electron beam when the X-ray source enters the capture section; a deflection unit for adjusting the direction of the emitted electron beam; and an X-ray target for enabling the electron beam to be focused at a predetermined X-ray focus and radiate the X-rays.

The deflection unit may be any one of a device using an electric or magnetic field method and a device using a combination thereof.

The terminal may control the direction of the electron beam based on the speed, exposure time and tube voltage of the X-ray source.

In order to accomplish the above object, the present invention provides a method of controlling a tomosynthesis system for digital X-ray imaging, including continuously moving during a scan period, and adjusting the direction of an emitted electron beam so that a uniform X-ray focus can be maintained in each capture section in which capture is performed; detecting, an image of X-rays having passed through an area of interest of an object in the capture section; and creating a 3D X-ray image by synthesizing detected X-ray images, and then displaying the 3D X-ray image.

The adjusting the direction of an emitted electron beam may include determining whether the X-ray source has entered the capture section; if the X-ray source has entered the capture section, emitting the electron beam from an electron gun of the X-ray source; and adjusting the direction of the emitted electron beam based on a preset target focus of the X-ray source under the control of a deflection unit.

The adjusting the direction of an emitted electron beam may include determining whether the X-ray source has entered the capture section; if the X-ray source has entered the capture section, emitting the electron beam using an electron gun of the X-ray source; adjusting the direction of the emitted electron beam based on a preset target focus of the X-ray source under the control of a deflection unit; and adjusting the location or coordinates of a collimator based on a preset value.

The adjusting the direction of an emitted electron beam may further include determining whether the X-ray source moves away from the capture section; and if the X-ray source moves away from the capture section, stopping the emission of the electron beam by the electron gun of the X-ray source.

The displaying the 3D X-ray projection image may include, if the scan period has terminated, creating the 3D X-ray projection image by synthesizing the detected X-ray images; and displaying the created 3D projection X-ray image.

BRIEF DESCRIPTION OF THE DRAWINGS

The above and other objects, features and advantages of the present invention will be more clearly understood from the following detailed description taken in conjunction with the accompanying drawings, in which:

FIG. 7 is a diagram showing an example of a method of controlling a tomosynthesis system according to an embodiment of the present invention.

DETAILED DESCRIPTION OF EXAMPLE EMBODIMENTS

Figure 1:
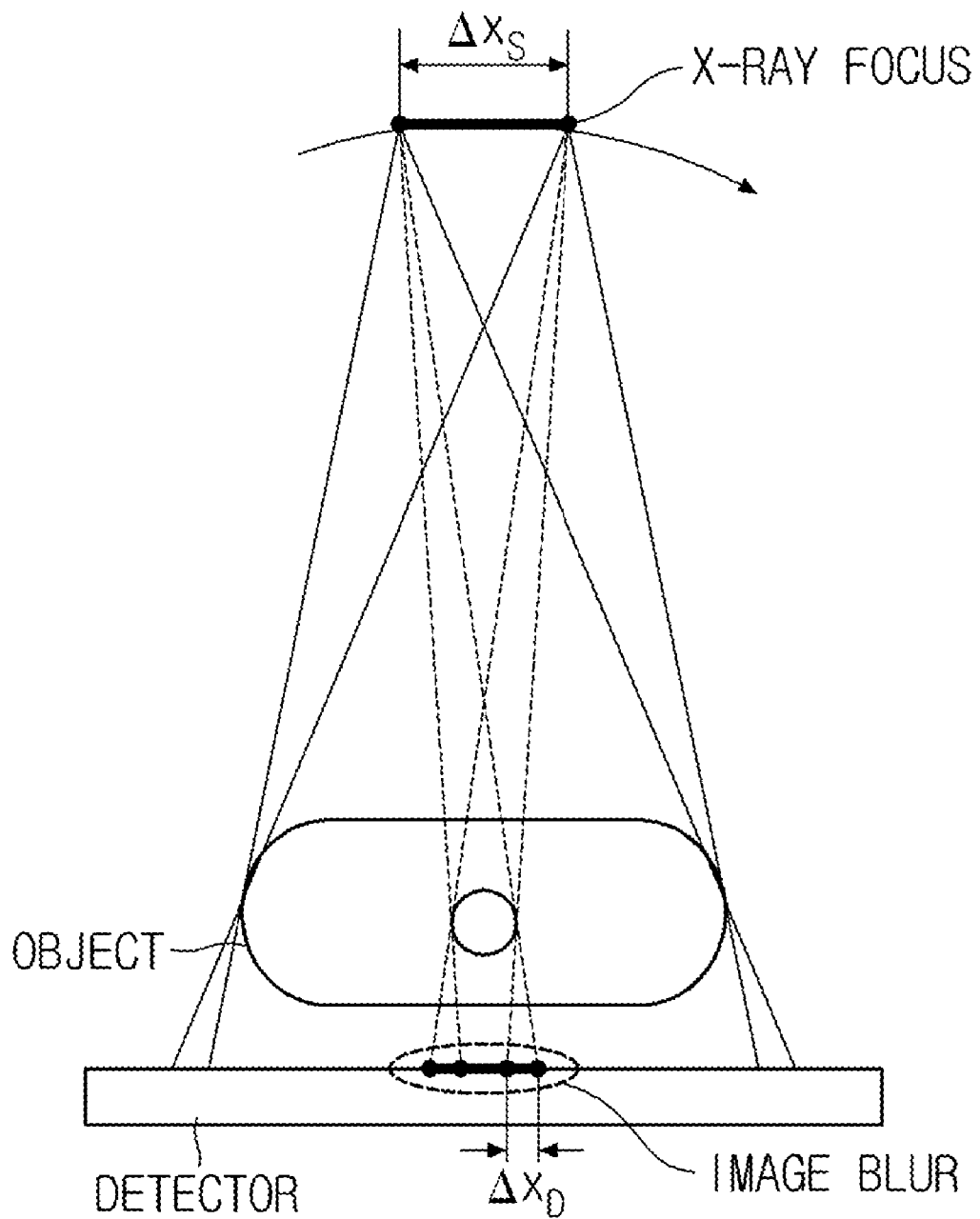
FIG. 1 is an exemplary diagram illustrating the principle of capturing which is performed while the X-ray source of a conventional tomosynthesis system continuously moves.

Reference now should be made to the drawings, in which the same reference numerals are used throughout the different drawings to designate the same or similar components.

A tomosynthesis system for digital X-ray imaging and a method of controlling the system according to an embodiment of the present invention will be described in detail below with reference to FIGS. 2 to 7. The present invention allows an X-ray source to continuously move during a scan period, and is intended to maintain a uniform X-ray focus in each capture section by adjusting the direction of an electron beam emitted by the electron gun of the X-ray source while the X-ray source continuously moves.

Figure 2:
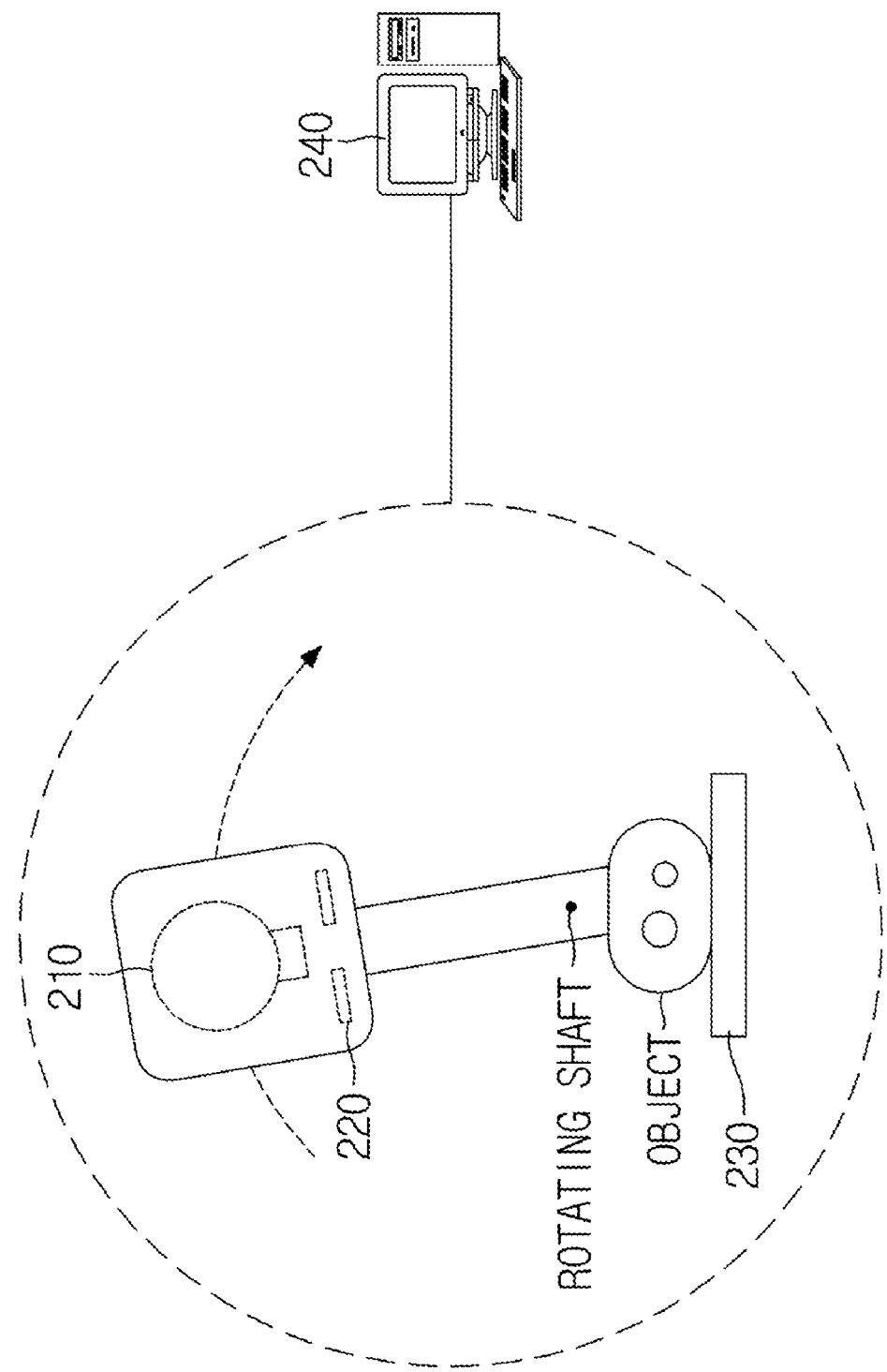
FIG. 2 is a schematic diagram showing an example of a tomosynthesis system according to an embodiment of the present invention.

FIG. 2 is a schematic diagram showing an example of a tomosynthesis system according to an embodiment of the present invention.

As shown in FIG. 2, the tomosynthesis system according to the embodiment of the present invention includes an X-ray source 210, a collimator 220, a detector 230, and a terminal 240. A method of operating such a tomosynthesis system will now be described.

An object to be captured is placed at a predetermined location first, and then X-rays are radiated onto the object using an X-ray tube or the X-ray source 210.

The detector 230 detects images of X-rays radiated by the X-ray source 210 and passing through an area of interest of the object. In this case, the detector 230 is aligned with the X-ray source 210, and captures X-ray images at various angles. In particular, during a scan period in which X-ray images are captured at various angles, the X-ray source 210 continuously moves. The same X-ray focus can be maintained in each of sections having a predetermined angular range by adjusting the direction of an electron beam, emitted by the electron gun of the X-ray source 210, for the section.

Figure 3:
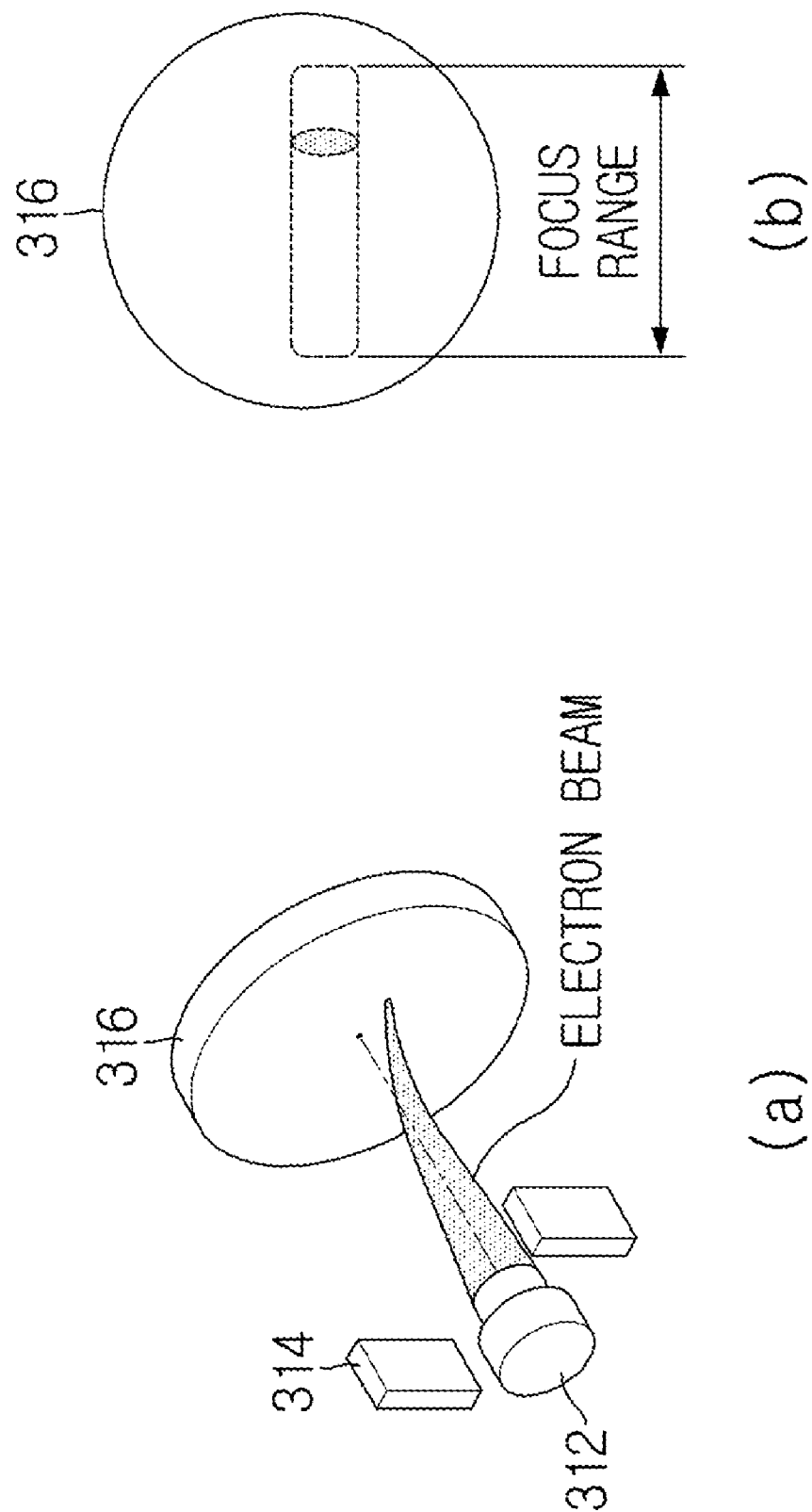
FIG. 3 is a diagram showing an example of the internal configuration of the X-ray source shown in FIG. 2.

FIG. 3 is a diagram showing an example of the internal configuration of the X-ray source 210 shown in FIG. 2.

As shown in FIG. 3, the X-ray source 210 according to the embodiment of the present invention may include a cathode unit or an electron gun 312, a deflection unit 314, and an anode unit or an X-ray target 316. For example, as shown in FIG. 3(a), the direction of an electron beam emitted by the cathode unit 312 is adjusted by applying different voltages to respective parts of the deflection unit 314.

Furthermore, as shown in FIG. 3(b), an electron beam emitted by the electron gun 312 is focused at a predetermined location of the X-ray target 316 by the deflection unit 314. The location of the X-ray target 316 at which the electron beam is focused is precisely adjusted within a predetermined focus range by adjusting the magnitude of the voltage.

Here, the deflection unit 314 may be a device for deflecting an electron beam using one of various methods, such as an electric field method and a magnetic field method, or a device using the combination thereof.

The terminal 240 creates a 3D projection image of the area of interest of the object based on the detected X-ray images, and displays the created 3D projection image.

In particular, the terminal 240 according to the embodiment of the present invention controls the deflection unit 314 so as to deflect an electron beam, and creates and provides a control signal for controlling the deflection unit 314 based on the speed, exposure time and tube voltage of the X-ray source 210.

Figure 4:
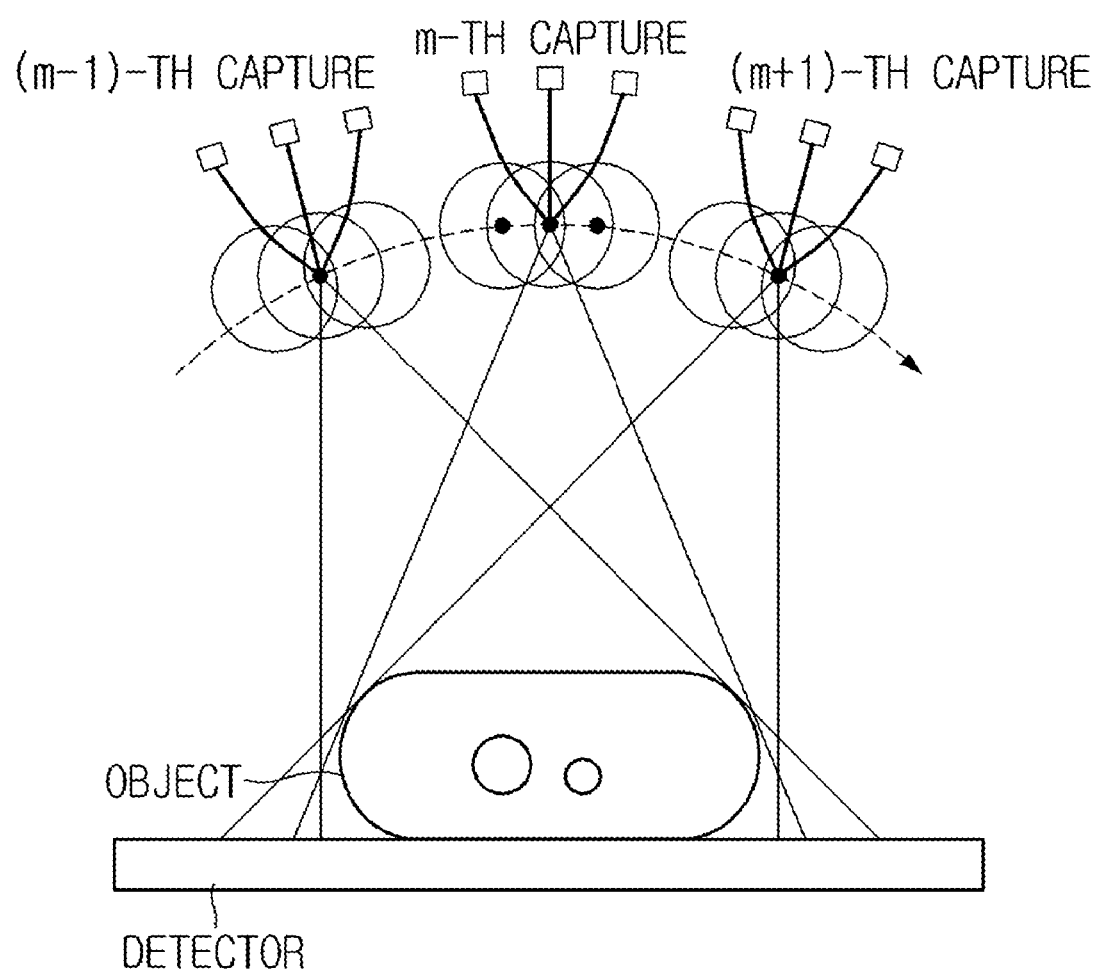
FIG. 4 is a first exemplary diagram illustrating the principle of capturing which is performed while the X-ray source of the tomosynthesis system according to the embodiment of the present invention continuously moves.

FIG. 4 is a first exemplary diagram illustrating the principle of capturing which is performed while the X-ray source of the tomosynthesis system according to the embodiment of the present invention continuously moves.

As shown in FIG. 4, it can be seen that in order to create a 3D projection image of a specific object, the X-ray source continuously moves while radiating X-rays in a single scan period in which X-ray images are detected at various angles.

For example, as shown in the drawing, when the X-ray source enters a capture section, particularly an (m−1)-th capture section or period, an electron beam focused on an X-ray target is deflected such that the X-ray source can maintain the same X-ray focus in this section even when the X-ray source moves while radiating X-rays. Thereafter, when the X-ray source moves away from this section, the X-ray source stops radiating X-rays.

Thereafter, when the X-ray source enters an m-th capture section, the electron beam focused on the X-ray target is deflected such that the X-ray source can maintain the same X-ray focus in this section even when the X-ray source moves while radiating X-rays. Thereafter, when the X-ray source moves away from this section, the X-ray source stops radiating X-rays.

Thereafter, when the X-ray source enters an (m+1)-th capture section, the electron beam focused on the X-ray target is deflected such that the X-ray source can maintain the same X-ray focus in this section even when the X-ray source moves while radiating X-rays. Thereafter, when the X-ray source moves away from this section, the X-ray source stops radiating X-rays.

Using the above-described method, N captures are performed during the overall scan period and the X-ray focus of the moving X-ray source is kept the same during the period, so that X-rays are radiated onto an object in a uniform direction within a relevant section.

Figure 5:
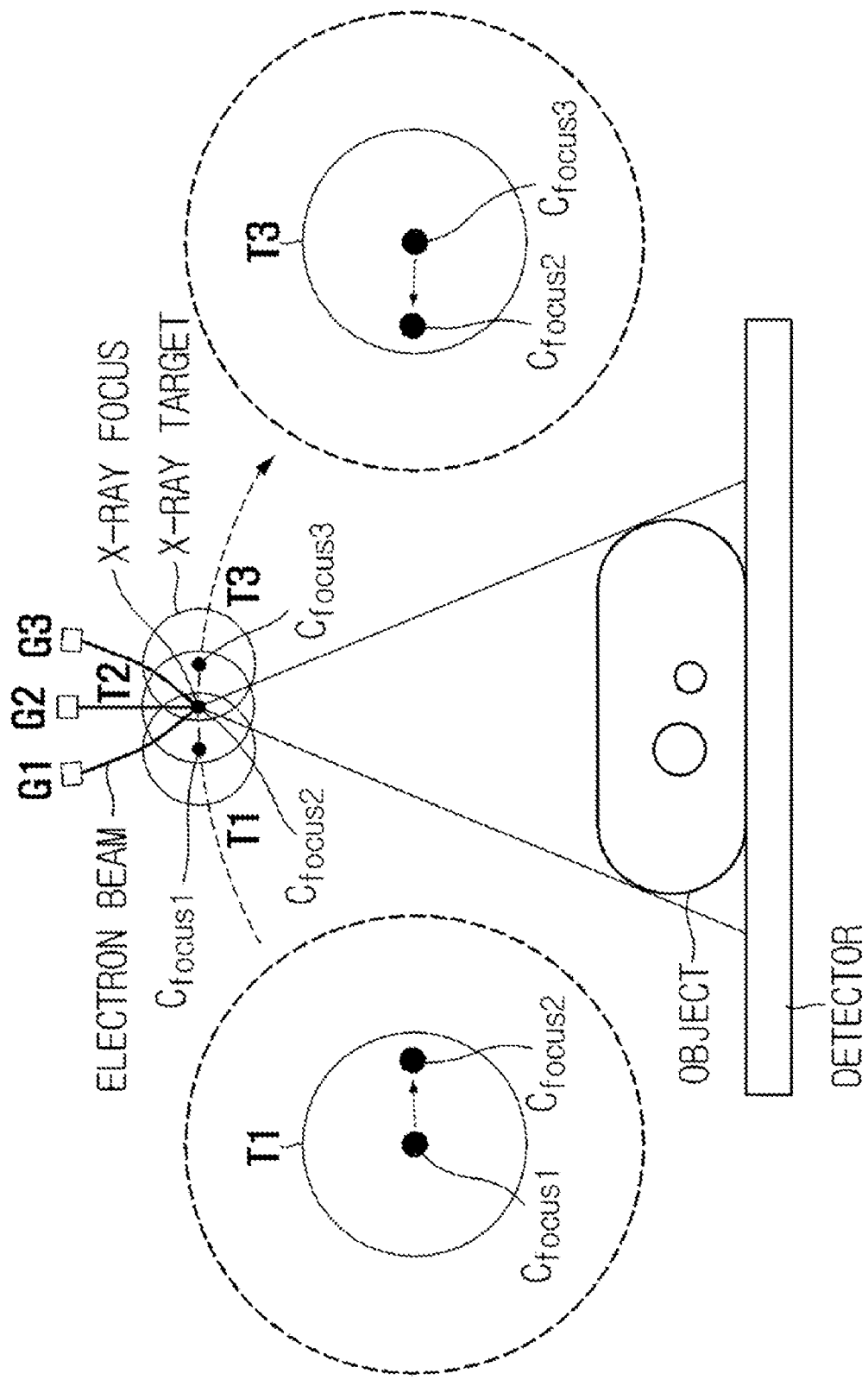
FIG. 5 is a second exemplary diagram illustrating the principle of capturing which is performed while the X-ray source of the tomosynthesis system according to the embodiment of the present invention continuously moves.

FIG. 5 is a second exemplary diagram illustrating the principle of capturing which is performed while the X-ray source of the tomosynthesis system according to the embodiment of the present invention continuously moves.

As shown in FIG. 5, it can be seen that X-rays are radiated onto an object in a uniform direction within a predetermined capture section. A specific location or specific coordinates of the X-ray source are set for each capture section, and the center of an X-ray target based on the preset location of the X-ray source is set as a target focus in the section.

The capture section may be determined by dividing a whole scan area by a preset capture angular range and the number of captures. The specific location of the X-ray source and the speed of the X-ray source may be obtained in the terminal by using the angular location information of the X-ray source, which is saved in an encoder included in a device rotating the X-ray source.

For example, when an X-ray source enters the capture section after the target focus of the X-ray source has been set, an electron beam is generated by the electron gun G1 of the X-ray source and the generated electron beam is deflected to be focused at a target focus $C_{focus2}$ instead of at a focus $C_{focus1}$, which is the center of an X-ray target T1.

As the X-ray source moves, the electron beam generated by an electron gun G2 is focused at the target focus $C_{focus2}$, which is the center of the X-ray target T2. In this case, the location or coordinates of the X-ray source is the preset location or coordinates, so that the control of an electron beam which is performed to deflect the electron beam is not performed.

Thereafter, as the X-ray source moves, the electron beam generated by an electron gun G3 is deflected to be focused at the target focus $C_{focus2}$ instead of at a focus $C_{focus3}$, which is the center of an X-ray target T3. Thereafter, when the X-ray source moves away from the capture section, the radiation of X-rays by the X-ray source stops.

Furthermore, X-rays radiated by the X-ray source may enter an object to be captured through the collimator 220 which is placed below the X-ray source. That is, an X-ray capture area is determined and the capture area or an area of interest is adjusted under the control of the collimator 220.

If such a collimator 220 is not used, unnecessary regions are captured and a plurality of captures is performed, so that the amount of X-rays to which a patient is exposed increases.

In general, the collimator 220 is configured to control a collimation area by controlling the gaps between several blades, and X-rays which do not pass through the gaps are absorbed by the blades which are made of high band gap atom material.

Figure 6:
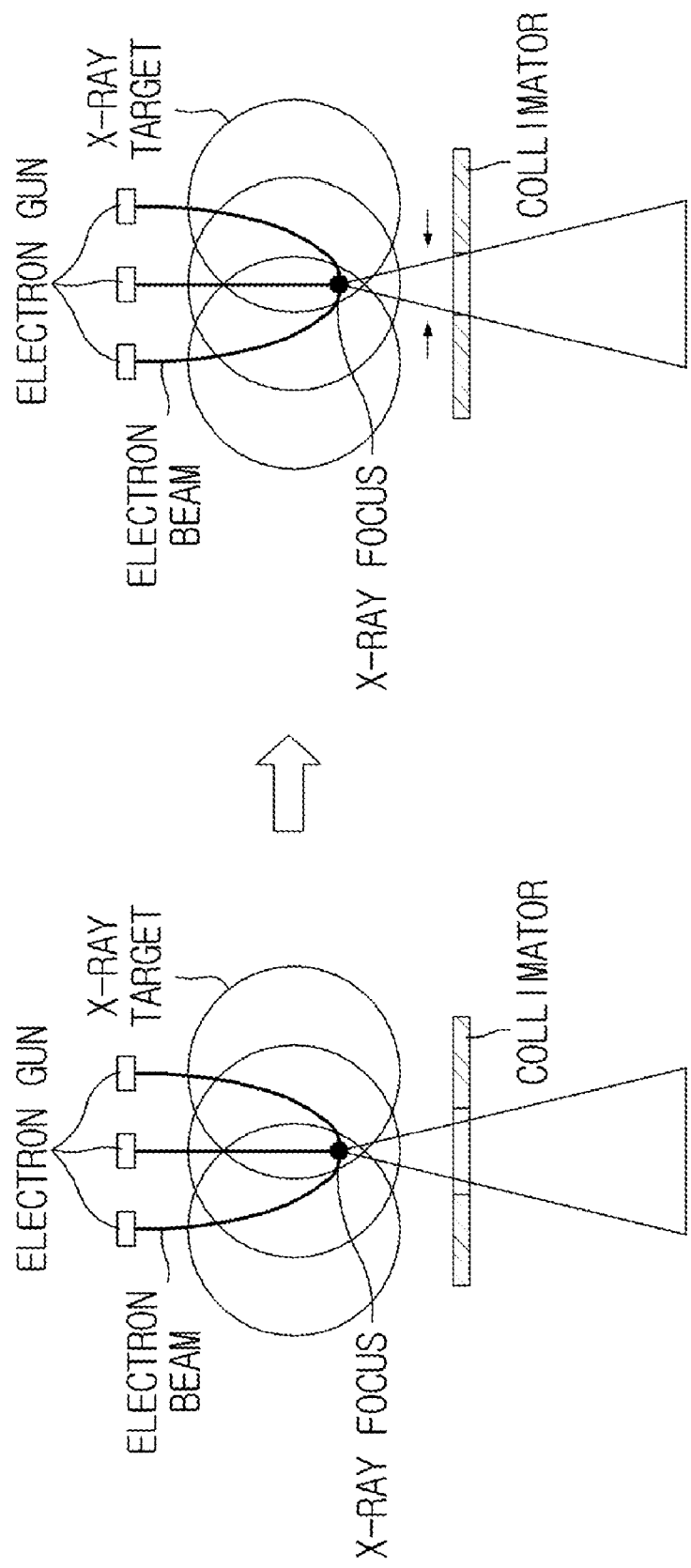
FIG. 6 is a diagram showing an example of a method of controlling a collimator according to an embodiment of the present invention.

FIG. 6 is a diagram showing an example of a method of controlling a collimator according to an embodiment of the present invention.

As shown in FIG. 6, the location or coordinates of the collimator according to the present invention is set in advance for a predetermined capture section because a relevant X-ray focus is the same in the same capture section. Thereafter, when an X-ray source enters a predetermined capture section, the collimator is controlled by moving it to the preset location or coordinates along the X or Y axis.

X-rays are made to enter an object to be captured by the collimator 220 that is controlled as described above, the X-rays passing through the object are detected by the detector 230, and the terminal can create an X-ray image by processing the detected signals using a processor.

FIG. 7 is a diagram showing an example of a method of controlling a tomosynthesis system according to an embodiment of the present invention.

As shown in FIG. 7, when an object to be captured is placed and then a scan is started, the X-ray source starts to move at a uniform speed at step S710. As the X-ray source moves, whether the X-ray source has entered a predetermined capture section is determined at step S720.

In this case, if the location where the scan starts corresponds to a capture section, the object can be captured even when the X-ray source does not move.

If the X-ray source has entered the capture section, an electron beam is emitted by the electron gun of the X-ray source at step S730, and the direction of the emitted electron beam is adjusted (deflected) based on the preset target focus of the X-ray source under the control of the deflection unit at step S740. Furthermore, according to a value set in advance, the location or coordinates of the collimator are also adjusted at step S750.

Thereafter, an X-ray image of the area of interest of the object is detected at step S760.

In contrast, if the X-ray source has not entered the capture section, the X-ray source continuously moves at step S710.

Thereafter, whether the X-ray source moves away from the corresponding capture section is periodically determined at step S770. If the X-ray source moves away from the corresponding capture section, the emission of the electron beam by the electron gun of the X-ray source stops, thereby stopping the radiation of X-rays at step S780.

In contrast, if the X-ray source does not move away from the corresponding capture section, whether the X-ray source moves away from the corresponding capture section is repeatedly determined during the process of detecting an X-ray image of the area of interest of the object while adjusting the direction of an electron beam radiated by the electron gun of the X-ray source and the location or coordinates of the collimator in the corresponding capture section.

Thereafter, whether a corresponding scan has been terminated is periodically determined at step S790. If the scan has terminated, a 3D projection image of the area of interest of the object is created based on the detected X-ray images and the created 3D projection image is displayed on the screen of the terminal at step S800.

In this case, if the location where the scan has terminated corresponds to the capture section, the capture of the object is performed even when the X-ray source does not move.

In contrast, if the scan has not terminated, whether the X-ray source has entered a capture section is determined at step S710, and then the following process is performed depending on the results of the determination.

The present invention is configured to maintain a uniform X-ray focus in each section by adjusting the direction of an electron beam emitted by the electron gun of the X-ray source while the X-ray source continuously moves, so that the present invention has the advantage of removing mechanical instability using the continuous movement of the X-ray source.

Furthermore, the present invention is configured to maintain a uniform X-ray focus in each section by adjusting the direction of an electron beam emitted by the electron gun of the X-ray source while the X-ray source continuously moves, so that the present invention has the advantage of preventing image blur from occurring and therefore improving the quality of images.

Furthermore, the present invention is configured to maintain a uniform X-ray focus in each section by adjusting the direction of an electron beam emitted by the electron gun of the X-ray source while the X-ray source continuously moves, so that the present invention has the advantage of reducing the scan time by continuously moving the X-ray source.

Furthermore, the present invention is configured to maintain a uniform X-ray focus in each section by adjusting the direction of an electron beam emitted by the electron gun of the X-ray source while the X-ray source continuously moves, so that the present invention has the advantage of shortening the scan time, thereby eliminating patients' pain and inconvenience.

The tomosynthesis system for digital X-ray imaging and the method of controlling the system according to the present invention may be varied and modified in various forms within the scope of the technical spirit of the present invention, and is not limited to the embodiments. Furthermore, the embodiments and the accompanying drawings are intended only to illustrate the present invention in detail, but are not intended to limit the technical spirit of the invention. It will be apparent to those skilled in the art that the present invention is not limited to the embodiments and the accompanying drawings because various modifications, additions and substitutions are possible without departing from the scope and spirit of the invention. The scope of the present invention should be determined based on not only the following claims but also equivalents of the claims.

What is claimed is:

1. A tomosynthesis system for digital X-ray imaging, comprising:
    an X-ray source configured to continuously move during a scan period and to maintain a uniform X-ray focus in each capture section in which capture is performed by adjusting a direction of an emitted electron beam;
    a detector for detecting an image of X-rays having passed through an area of interest of an object in the capture section; and
    a terminal for controlling the adjustment of direction of the electron beam, and creating a three-dimensional (3D) X-ray image by synthesizing detected X-ray images and then displaying the 3D X-ray image.

2. The tomosynthesis system as set forth in claim 1, wherein the X-ray source comprises:
    an electron gun for emitting the electron beam when the X-ray source enters the capture section;
    a deflection unit for adjusting the direction of the emitted electron beam; and
    an X-ray target for enabling the electron beam to be focused at a predetermined X-ray focus and radiate the X-rays.

3. The tomosynthesis system as set forth in claim 2, wherein the deflection unit is any one of a device using an electric or magnetic field method and a device using a combination thereof.

4. The tomosynthesis system as set forth in claim 1, wherein the terminal controls the direction of the electron beam based on speed, exposure time and tube voltage of the X-ray source.

5. A tomosynthesis system for digital X-ray imaging, comprising:
    an X-ray source configured to continuously move during scan period and to maintain a uniform X-ray focus in each capture section in which capture is performed by adjusting a direction of an emitted electron beam;
    a collimator configured such that it is controlled by moving it based on a preset location or preset coordinates in the capture section;
    a detector for detecting an image of X-rays having passed through an area of interest of an object in the capture section; and
    a terminal for controlling the adjustment of direction of the electron beam, and creating a 3D X-ray image by synthesizing detected X-ray images and then displaying the 3D X-ray image.

6. The tomosynthesis system as set forth in claim 5, wherein the collimator enables the X-rays to enter the area of interest of the object by controlling gaps between blades.

7. The tomosynthesis system as set forth in claim 5, wherein the X-ray source comprises:
    an electron gun for emitting the electron beam when the X-ray source enters the capture section;
    a deflection unit for adjusting the direction of the emitted electron beam; and
    an X-ray target for enabling the electron beam to be focused at a predetermined X-ray focus and radiate the X-rays.

8. The tomosynthesis system as set forth in claim 7, wherein the deflection unit is any one of a device using an electric or magnetic field method and a device using a combination thereof.

9. The tomosynthesis system as set forth in claim 5, wherein the terminal controls the direction of the electron beam based on speed, exposure time and tube voltage of the X-ray source.

10. A method of controlling a tomosynthesis system for digital X-ray imaging, comprising:
    continuously moving during a scan period, and adjusting a direction of an emitted electron beam so that a uniform X-ray focus is maintained in each capture section in which capture is performed;
    detecting an image of X-rays having passed through an area of interest of an object in the capture section; and
    creating a 3D X-ray image by synthesizing detected X-ray images, and then displaying the 3D X-ray image.

11. The method as set forth in claim 10, wherein the adjusting a direction of an emitted electron beam comprises:
    determining whether the X-ray source has entered the capture section;
    if the X-ray source has entered the capture section, emitting the electronic beam from an electron gun of the X-ray source; and
    adjusting the direction of the emitted electron beam based on a preset target focus of the X-ray source under the control of a deflection unit.

12. The method as set forth in claim 10, wherein the adjusting a direction of an emitted electron beam comprises:
 determining whether the X-ray source has entered the capture section;
 if the X-ray source has entered the capture section, emitting the electronic beam using an electron gun of the X-ray source;
 adjusting the direction of the emitted electron beam based on a preset target focus of the X-ray source under the control of a deflection unit; and
 adjusting a location or coordinates of a collimator based on a preset value.

13. The method as set forth in claim 11, wherein the adjusting a direction of an emitted electron beam further comprises:
 determining whether the X-ray source moves away from the capture section; and
 if the X-ray source moves away from the capture section, stopping the emission of the electron beam by the electron gun of the X-ray source.

14. The method as set forth in claim 10, wherein the displaying the 3D X-ray projection image comprises:
 if the scan period has terminated, creating the 3D X-ray projection image by synthesizing the detected X-ray images; and
 displaying the created 3D projection X-ray image.

\* \* \* \* \*